United States Patent [19]
Takahashi et al.

[11] 4,060,120
[45] Nov. 29, 1977

[54] INVESTMENT CASTING PROCESS OF CHROMIUM-COBALT AND/OR NICKEL ALLOYS

[75] Inventors: Shigeo Takahashi; Michio Ito, both of Shioziri; Sakae Nagasawa, Matsumoto; Sigeo Suzuki, Nagoya, all of Japan

[73] Assignees: Matsumoto Dental College, Shiroziri; Sumitomo Chemical Company, Limited, Osaka, both of Japan

[21] Appl. No.: 645,895

[22] Filed: Dec. 31, 1975

[51] Int. Cl.$^2$ .................. B22D 21/06; B22D 13/00
[52] U.S. Cl. .................. 164/35; 164/118; 164/DIG. 3; 164/DIG. 4
[58] Field of Search .................. 164/34, 35, 36, 114, 164/118, 121, DIG. 3, DIG. 4

[56] References Cited
U.S. PATENT DOCUMENTS

| 3,192,583 | 7/1965 | Fryrear, Jr. | 164/34 |
| 3,616,840 | 11/1971 | Dunlop | 164/34 X |
| 3,685,115 | 8/1972 | Scott | 164/34 X |
| 3,698,468 | 10/1972 | Hudson | 164/DIG. 4 X |
| 3,716,418 | 2/1973 | Kochavi | 164/DIG. 4 |

FOREIGN PATENT DOCUMENTS 770,527   3/1957   United Kingdom .................. 164/35

*Primary Examiner*—Ronald J. Shore
*Attorney, Agent, or Firm*—Birch, Stewart, Kolasch and Birch

[57] ABSTRACT

An improved investment casting process for producing dental restorations, particularly a dental crown, comprising the steps of fixing a wax pattern onto a truncated cone in a metallic ring having a lining of a cushioning material, pouring an investment material into the space around the wax pattern in the metallic ring, drying the resultant product, melting out the invested wax pattern, curing the resultant product at a temperature of 700° to 950° C for 20 to 150 minutes to give a mold, fixing the mold thus obtained to a centrifugal casting machine and casting a molten chromium-cobalt and/or nickel alloy in the mold maintained at a temperature of 100° to 500° C.

5 Claims, 6 Drawing Figures

FIG. 1
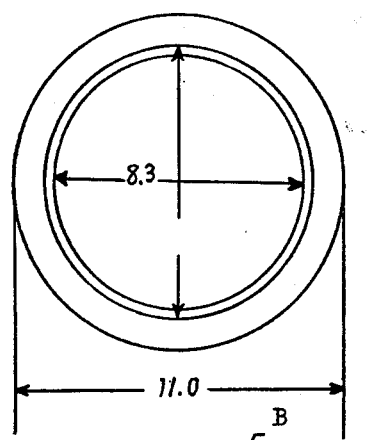
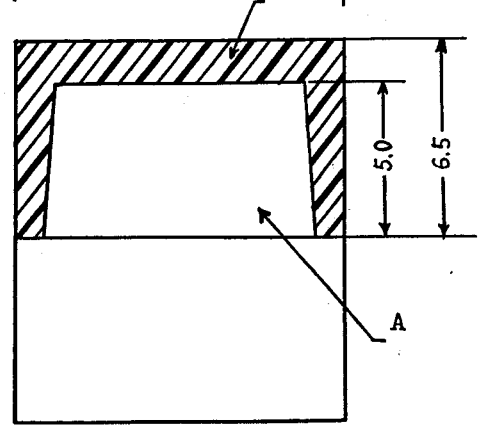
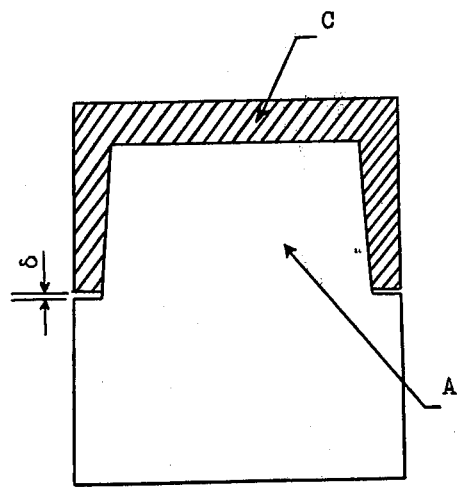
FIG. 2        FIG. 3

INVESTMENT CASTING PROCESS OF CHROMIUM-COBALT AND/OR NICKEL ALLOYS

BACKGROUND AND SUMMARY OF THE INVENTION

The present invention relates to an improved investment casting process of chromium-cobalt and/or nickel alloys for producing dental restorations. More particularly, it relates to a process for producing a dental crown suitable for baking porcelain thereon from chromium-cobalt and/or nickel alloys by a centrifugal casting process wherein the mold is made from a investment material.

Recently, there is increased use in the applications of chromium-cobalt and/or nickel alloys for cast dental restorations instead of noble metal alloys. Their popularity is attributed to their low cost, excellent stability in vivo and excellent strength and durability.

According to the conventional lost-wax casting process, the metal crown useful as artificial teeth or a part thereof is produced by preparing a pattern of the metal crown by a wax, pouring a creamy investment material around the wax pattern, melting out the invested wax pattern to form the mold, and casting a molten alloy into the cavity of the mold, which is formed after melting out the wax pattern. However, when a metal having a high melting point is used, this process can hardly produce a product having excellent dimensional accuracy at the corners or margins thereof as well as good surface smoothness. Particularly, the metallic material used for the production of the metal crown suitable for baking porcelain thereon should be tolerant to such a high baking temperature of the porcelain, e.g., about 1,000° C without losing the excellent dimensional accuracy, and therefore, the metallic material is naturally required to have a high melting point, which induces the shrinkage of the metallic material and the reaction thereof with the investment material during the casting operation. Moreover, the dimensional accuracy at the corners or margins of the castings and the smoothness of the surface thereof affect the workability for making artificial teeth therefrom as well as the properties of the resulting artificial teeth.

Under the circumstances, the present inventors have intensively studied to find an improved process for casting dental alloys, particularly dental chromium-cobalt and/or nickel alloys without producing the surface roughening of the castings and without lowering the dimensional accuracy thereof and thus producing the metal crown for artificial teeth having excellent properties and excellent durability. As a result of the present invention it has been found that the desired product can be produced by subjecting the chromium-cobalt and/or nickel alloys to a centrifugal casting process under specific conditions.

An object of the present invention is to provide an improved investment casting process of chromium-cobalt and/or nickel alloys for producing dental restorations having excellent dimensional accuracy and surface smoothness.

Another object of the present invention is to provide improved process for producing a dental crown by a centrifugal casting process.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

The investment casting of the chromium-cobalt and/or nickel alloys is usually carried out by fixing a wax pattern onto a truncated cone, which forms the reservoir for the molten metal in casting, in a metallic ring, which has a lining of a cushioning material such as asbestos, pouring a creamy investment material, which is prepared by mixing an investment material with water and milling the mixture, into the metallic ring, drying the resultant, melting out the invested wax pattern by heating in a furnace (e.g. an electric furnace), keeping the resultant at a temperature of 800° C or higher to cure the mold, fixing the resulting mold maintained at such high temperatures to a high-frequency centrifugal casting machine, and casting a molten chromium-cobalt and/or nickel alloy in the mold which is heated at the red-hot state. However, according to this conventional process, the castings thus obtained have inferior dimensional accuracy ($\delta > 0.5\%$) and inferior surfaces due to the reaction of the casting material (alloys) with the investment material.

According to the present invention, such defects can be overcome by carrying out the curing of the mold at a temperature of 700° to 950° C for 20 to 150 minutes and further by carrying out the casting of the alloy while keeping the temperature of the mold at 100° to 500° C, by which there can be obtained the desired metal crown of the chromium-cobalt and/or nickel alloys having an excellent dimensional accuracy and an excellent surface smoothness.

The cushioning materials used in the present invention include any commercially available materials, for instance, asbestos or ceramic fibers, such as alumina fibers (e.g. Saffil, trade name of the product of ICI), zirconia fibers (e.g. Zircar, trade name of the product of ICI), silica-alumina fibers (e.g. Kaowool, trade name of the product of Babcock & Wilcox Co.).

The investment materials used in the present invention include any commercially available calcium phosphate type investment materials, for instance, Ceravest (trade name of the product of GC Company), Ceramigold (trade name of the product of Whip-Mix Co.), Hi-Vest (trade name of the product of Shofu Dental Mfg. Co. Ltd.), and Crown-Vest (trade name of the product of Sankin Kogyo Co., Ltd.).

The chromium-cobalt and/or nickel alloys used in the present invention as the casting material include any commercially available alloys. The alloys contain no less than 80% by weight of chromium, cobalt and/or nickel combined. These alloys may contain from two to seven major constituents plus several minor ingredients. The major metals may include chromium (10 to 70% by weight), cobalt (20 to 80% by weight), nickel (0.5 to 90% by weight) and molybdenum (4 to 12% by weight). Suitable examples of the chromium-cobalt and/or nickel alloys are shown in the following Table 1.

Table 1

| Product (trade name) | Company | Cr | Co | Ni | Fe | Mo | Mn | Cu | Others | Hardness ($H_B$) | Tensile strength (Kg/mm$^2$) | Elongation (%) | Melting point (° C) |
|---|---|---|---|---|---|---|---|---|---|---|---|---|---|
| Cobalium | Yada Chemical Co., Ltd. | 25 | 50 | 17 | 2 | 4 | — | — | 2 | 270–290 | 80–83 | 4–6 | 1350–1380 |
| Sankolium H | Sankin Kogyo Co. Ltd. | >20 | 57 | >3 | — | — | — | — | 17 | 314 | 99.2 | 5 | 1390 |
| Sankolium M | " | >20 | 57 | 3 | — | — | — | — | 17 | 242 | 103 | 7.5 | 1400 |
| Sankolium S | " | >20 | — | 67 | — | — | — | — | 13 | 130 | 61.9 | 20 | 1380 |
| Sankolium US | " | 10 | — | 90 | — | — | — | — | — | 110 | 38.2 | 15 | 1300 |
| Washilium H | Kamemizu Chemical Co., Ltd. | 28 | 60 | — | — | 12 | — | — | — | 385 ($H_V$) | 86 | 4.5 | 1370 |
| Washilium M | " | 30 | 57 | 3 | — | 10 | — | — | — | 310 ($H_V$) | 73 | 8.5 | 1330 |
| Washilium S | " | 23 | 20 | 50 | — | — | 3 | 4 | — | 188 ($H_V$) | 58 | 19 | 1280 |
| Nobilium | Nobilium Co. | 30 | 60 | 1 | — | 5 | — | — | 4 | 360 ($H_V$) | 100 | — | 1350 |

Thus, the present invention provides an improved process for investment casting of dental alloys, comprising fixing a wax pattern onto a truncated cone in a metallic ring, which has a lining of a cushioning material, pouring an investment material into the space around the wax pattern in the metallic ring, drying the resultant, melting out the invested wax pattern and simultaneously curing the investment material by heating at a temperature of 700° to 950° C to form a mold, fixing the resulting mold to a conventional centrifugal casting machine, and casting a molten chromium-cobalt and/or nickel alloy in the mold maintained at a temperature of 100° to 500° C preferably 100° to 400° C.

According to the low temperature casting process of the present invention, Nobilium alloys (made by Nobilium Co.) or other commercially available, dental chromium-cobalt and/or nickel alloys, which have been considered to be difficult to cast by the conventional investment casting process, can easily be casted to give the desired, practically usable metal crown suitable for artificial teeth having an excellent smooth surface and an excellent dimensional accuracy.

In the present process, the metallic ring having a lining of a cushioning material may be replaced by a ringless or flexible ring type vessel, but the metallic ring is the most suitable one from the viewpoint of safety in the centrifugal casting process. In the present invention, the curing of the mold is carried out at a temperature of 700° to 950° C, and therefore, any combustible and volatile materials contained in the investment materials and the cushioning materials are lost from the mold. Accordingly, when the molten alloys are casted in the mold at a temperature of 100° to 500° C, the cracking thereof due to the heat shock can be prevented and further the excellent dimensional accuracy, which has never been achieved by the conventional products, can be achieved by the suitable combination of the shrinkage of the alloys and the expansion coefficient of the cushioning material. The present invention can be used not only for producing dental prothesis but also for producing metallic materials for implant, and for parts of machines made of metals having a high melting point which can not be produced by conventional mechanical cutting and processing and further is required to have a high chemical resistance.

BRIEF DESCRIPTION OF THE DRAWINGS

The present invention will become more fully understood from the detailed description given hereinbelow and the accompanying drawings which are given by way of illustration only, and thus are not limitative of the present invention, and wherein, FIG. 1 shows a plane view of only the mold part of the full-cast crown mold and FIG. 2 shows a sectional view of the central part of a full-cast crown mold made from a wax;

FIG. 3 shows a position for measuring the dimensional accuracy ($\delta$), i.e. the gap between the full-cast crown mold and the obtained castings. In FIG. 2, A is a metallic model, the cross section B is a wax pattern and the cross section C is the obtained castings.

In FIGS. 4–6, D is a metallic model, E is a pontic (i.e. a dummy), the cross section F is a wax pattern and the cross section G is the obtained castings. In FIGS. 1–6, the unit of the numeral is millimeter.

EXAMPLE 1

Figure 4:
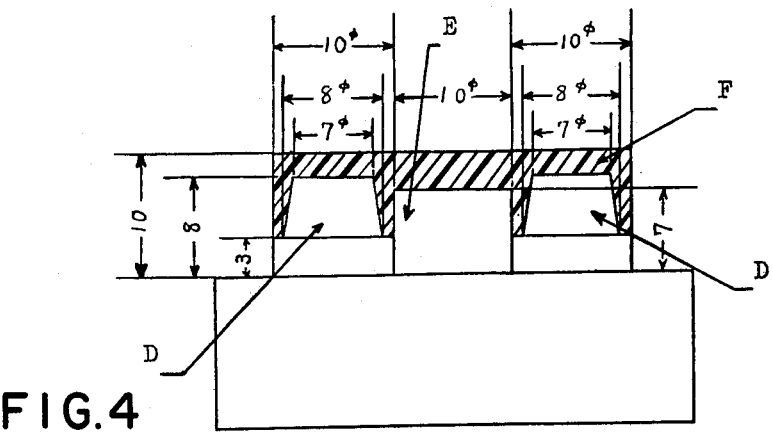
FIG. 4 shows a sectional view of the central part of a mold for a bridge missing one piece.
Figure 5:
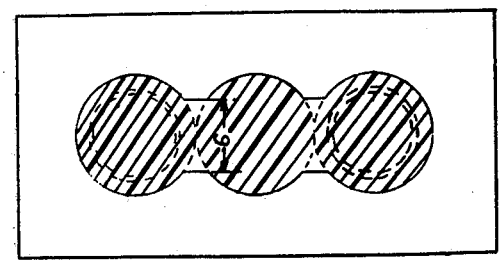
FIG. 5 shows a plane view of the mold and FIG. 6 shows a position for measuring the dimensional accuracy ($\delta$), i.e. the gap between the mold for bridge missing one piece and the obtained castings.
Figure 6:
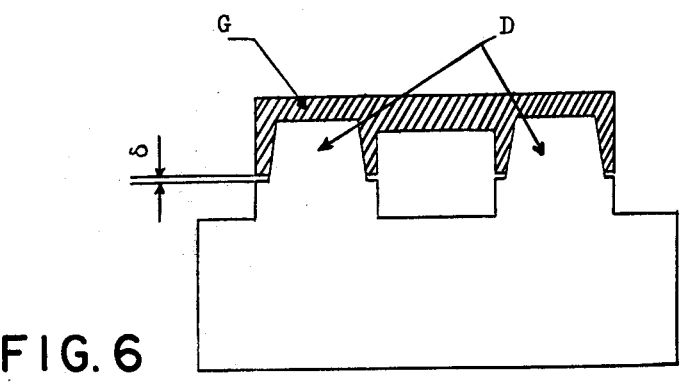

Blue-Inlay-Wax (made by GC Company) is molten in a temperature controlled bath (55° C) and the molten wax is added to a full-cast crown mold as shown in FIG. 2 at a constant pressure of 8 kg/cm$^2$.G using an oil pressure pump to prepare a wax pattern. The wax pattern thus obtained is fixed onto a conical crucible in a metallic ring having a lining (thickness: 1 mm) of a hygroscopic silica-alumina fiber (Kaowool, made by Babcock & Wilcox Co.), and thereto an alkaline investment material: Hi-Vest (made by Shofu Dental Mfg. Co., Ltd.) is poured in a vacuum. The resultant is dried and heated at 300° C for 30 minutes to melt out the wax pattern and then heated at 900° C for 30 minutes to give a mold.

The mold thus obtained is fixed into a high-frequency centrifugal casting machine (made by Unique Koden Lab.), and therein a chromium-cobalt-nickel alloy: Nobilium (made by Nobilium Co., Ltd.; nominal composition: Cr: 30, Co: 60, Ni: 1, Mo: 5, others: 4) is casted. The temperature of the mold is lowered to 200° C and kept for 30 minutes at that temperature, and then the alloy is molten at a high frequency and subjected to the centrifugal casting at a temperature of 1450° C. The castings thus obtained have a dimensional accuracy ($\delta$) at the corner and margin of less than 50 $\mu$ (less than 0.05%) (the data are an average of those measured at five positions of the castings) and an excellent surface smoothness (no reaction of the alloy with the investment material is observed).

EXAMPLE 2

Violet-Inley-Wax (made by GC Company) is molten in a temperature controlled bath (55° C) and the molten wax is added a mold for bridge missing one piece as shown in FIG. 2 to prepare a wax pattern. The wax pattern thus obtained is treated in the same manner as described in Example 1 excepting that an acidic investment material: Ceravest (made by GC Company) is used instead of the alkaline investment material to give a mold.

Using the mold thus obtained, the same alloy: Nobilium as in Example 1 is subjected to the centrifugal casting in the same manner as described in Example 1 excepting that the temperature of the mold is kept at 750° C for 120 minutes and is lowered to 350° C and kept for 30 minutes at the temperature, and then the molten alloy is subjected to the centrifugal casting at a temperature of 1500° C. The castings of bridge thus obtained have a dimensional accuracy ($\delta$) of less than 0.15 mm (less than 0.1%) (the data are an average of those measured at five positions of the castings) and an excellent surface smoothness (there is no problem in the flowing of the molten alloy into the mold).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. In an investment casting process for producing dental restorations having excellent dimensional accuracy and excellent surface smoothness by the steps of fixing a wax pattern onto a truncated cone in a metallic ring having a lining of a cushioning material, pouring an investment material into the space around the wax pattern in the metallic ring, drying the resultant product, melting out the invested wax pattern, curing the resultant product to give a mold, fixing the mold to a centrifugal casting machine and casting a molten chromium-cobalt and/or nickel alloy in the mold, wherein the improvement comprises curing the mold by heating it at a temperature of 700° to 950° C for 20 to 150 minutes and centrifugally casting the alloy while maintaining the temperature of the mold at 100° to 500° C.

2. The investment casting process according to claim 1, wherein the centrifugal casting of the alloy is carried out at a temperature of the mold of 100° to 400° C.

3. The investment casting process according to claim 1, wherein the dental restoration is a dental crown.

4. The investment casting process according to claim 1, wherein the alloy contains as the major constituents 10 to 70% by weight of chromium, 20 to 80% by weight of cobalt and/or 0.5 to 90% by weight of nickel.

5. The investment casting process according to claim 1, wherein the investment material is a composition of a calcium phosphate.

* * * * *